(12) United States Patent
Leang

(10) Patent No.: US 12,264,348 B2
(45) Date of Patent: *Apr. 1, 2025

(54) MICROORGANISM WITH KNOCK-IN AT ACETOLACTATE DECARBOXYLASE GENE LOCUS

(71) Applicant: LanzaTech, Inc., Skokie, IL (US)

(72) Inventor: Ching Leang, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,636

(22) Filed: May 2, 2023

(65) Prior Publication Data

US 2023/0348886 A1 Nov. 2, 2023

Related U.S. Application Data

(62) Division of application No. 17/303,677, filed on Jun. 4, 2021, now Pat. No. 11,760,989.

(60) Provisional application No. 63/035,739, filed on Jun. 6, 2020.

(51) Int. Cl.
| | |
|---|---|
| *C12N 9/88* | (2006.01) |
| *C12N 9/10* | (2006.01) |
| *C12P 5/00* | (2006.01) |
| *C12P 5/02* | (2006.01) |
| *C12P 7/04* | (2006.01) |
| *C12P 7/18* | (2006.01) |
| *C12P 7/26* | (2006.01) |
| *C12P 7/30* | (2006.01) |
| *C12P 7/42* | (2006.01) |
| *C12P 7/6409* | (2022.01) |

(52) U.S. Cl.
CPC ............. *C12N 9/88* (2013.01); *C12N 9/1029* (2013.01); *C12N 9/13* (2013.01); *C12P 5/007* (2013.01); *C12P 5/026* (2013.01); *C12P 7/04* (2013.01); *C12P 7/18* (2013.01); *C12P 7/26* (2013.01); *C12P 7/30* (2013.01); *C12P 7/42* (2013.01); *C12P 7/6409* (2013.01); *C12Y 208/03* (2013.01); *C12Y 401/01001* (2013.01); *C12Y 401/01005* (2013.01)

(58) Field of Classification Search
CPC ................. C12P 7/42; C12P 7/26; C12N 9/88
See application file for complete search history.

(56) References Cited

U.S. PATENT DOCUMENTS 11,760,989 B2 * 9/2023 Leang ...................... C12P 7/42
435/134

FOREIGN PATENT DOCUMENTS

| CN | 106190936 A | 12/2016 |
| JP | 2018530342 A | 10/2018 |
| WO | 2022066997 A1 | 3/2022 |

OTHER PUBLICATIONS

Extended European Search Report issued in corresponding European Patent Application No. 21817031.4, dated Apr. 29, 2024, 10 pages.

* cited by examiner

Primary Examiner — Tekchand Saidha

(57) ABSTRACT

Provided herein is a genetically engineered microorganism comprising knock-in of DNA at an acetolactate decarboxylase gene locus. Replacement of the acetolactate decarboxylase gene with DNA encoding one or more native or nonnative enzymes confers certain advantages, including fermentation stability and increased production of native and nonnative products from gaseous substrates.

21 Claims, 4 Drawing Sheets
Specification includes a Sequence Listing.

```
                              SEQUENCE LISTING

Sequence total quantity: 8
SEQ ID NO: 1            moltype = DNA  length = 160
FEATURE                 Location/Qualifiers
misc_feature            1..160
                        note = Region containing PbudA promoter, Clostridium
                         autoethanogenum
source                  1..160
                        mol_type = other DNA
                        organism = synthetic construct
SEQUENCE: 1
aatcatatat tgtaattatt tttaattatg ttggcaaaat tgaaattgtc actgaaacac    60
ctctaaatgt tttaaataca tatgtttaat tattgtgaca gattctaata gtagaaagta   120
gaaatttgct atgttataat gacatagagg tgaatgtaat                         160

SEQ ID NO: 2            moltype = DNA  length = 165
FEATURE                 Location/Qualifiers
misc_feature            1..165
                        note = Pfer promoter, Clostridium autoethanogenum
source                  1..165
                        mol_type = other DNA
                        organism = synthetic construct
SEQUENCE: 2
gctcactatc tgcggaacct gcctccttat ctgataaaaa atattcgctg catctttgac    60
ttgttatttt ctttcaaatg cctaaaatta tcttttaaaa ttataacaaa tgtgataaaa   120
tacaggggat gaaaacatta tctaaaaatt aaggaggtgt tacat                   165

SEQ ID NO: 3            moltype = DNA  length = 720
FEATURE                 Location/Qualifiers
misc_feature            1..720
                        note = budA, Clostridium autoethanogenum
source                  1..720
                        mol_type = other DNA
                        organism = synthetic construct
SEQUENCE: 3
atggatgatg aggtgaaagt cccaaaccat atatatcaaa tgtctacaat aaatgcactt    60
gtttcggggc tgtatgatgg ctgtgtttca ttatctaaac ttcttaaaaa aggaaacttt   120
ggtataggta cttttaaagg tctagatggt gaactaactc tttaaatgg aacttttat    180
aggactaaac ctgatggcag cgtatacgta tgttccaaaa acgtatccgt tccttttgct   240
gtagtcactg aactggaaaa ttataatact tataatattc aaaatcgtac ttcttatgaa   300
gatataagaa aagaattgga cagctttata gaaagcaaaa atatattta tgcttttctat   360
atggaaggta aatttaatta tgtaaaaaca cgtactgttg taaaacagaa tatgccttat   420
aagcctatgg ctgaagttgt taaagatcag cctatgtttg aatataacgg tgttgatgga   480
tatgtggttg gattaggtg tcctgattat gttgaaggcc ttaatgtccc tggatatcat   540
tttcatttca taaataaaga taagaaattt ggtggacata taagtgaatt ttccattgaa   600
aatgcgaagg tttatgtaca gaactgttct tgctttagga tggaacttcc taaaaatgaa   660
agttttata atatggaagt acaagataga aacgatgaga taacaagtgt tgaaaaataa   720

SEQ ID NO: 4            moltype = DNA  length = 1056
FEATURE                 Location/Qualifiers
misc_feature            1..1056
                        note = secAdh, Clostridium autoethanogenum
source                  1..1056
                        mol_type = other DNA
                        organism = synthetic construct
SEQUENCE: 4
atgaaaggtt ttgcaatgtt aggtattaac aaattaggat ggattgaaaa gaaaaaccca    60
gtgccaggtc cttatgatgc gattgtacat cctctagctg tatccccatg tacatcagat   120
atacatacgg ttttttgaagg agcacttggt aatagggaaa atatgatttt aggccatgaa   180
gctgtaggtg aaatagccga agttggcagc gaagttaaag atttaaagt tggcgataga   240
gttatcgtac catgcacaac acctgactgg agatctttag aagtccaagc tggttttcag   300
```

```
cagcattcaa acggtatgct tgcaggatgg aagttttcca attttaaaga tggtgtattt    360
gcagattact ttcatgtaaa cgatgcagat atgaatcttg ccatactccc agatgaaata    420
cctttagaaa gtgcagttat gatgacagac atgatgacta ctggttttca tggagcagaa    480
cttgcagaca taaaaatggg ctccagcgtt gtagtaattg gtataggagc tgttggatta    540
atgggaatag ccggttccaa acttcgagga gcaggcagaa ttatcggtgt tggaagcaga    600
cctgttttgtg ttgaaacagc taaattttat ggagcaactg atattgtaaa ttataaaaat    660
ggtgatatag ttgaacaaat catggactta actcatggta aaggtgtaga ccgtgtaatc    720
atggcaggcg gtggtgctga aacactagca caagcagtaa ctatggttaa acctggcggc    780
gtaatttcta acatcaacta ccatggaagc ggtgatactt taccaatacc tcgtgttcaa    840
tgggctgcg gcatggctca caaaactata agaggaggat tatgccccgg cggacgtctt    900
agaatggaaa tgctaagaga tcttgttcta tataaacgtg ttgatttgag taaacttgtt    960
actcatgtat ttgatggtgc agaaaatatt gaaaaggccc ttttgcttat gaaaaataag   1020
ccaaaagatt taattaaatc agtagttaca ttctaa                              1056

SEQ ID NO: 5         moltype = DNA  length = 2613
FEATURE              Location/Qualifiers
misc_feature         1..2613
                     note = adhE1, Clostridium autoethanogenum
source               1..2613
                     mol_type = other DNA
                     organism = synthetic construct
SEQUENCE: 5
atgaaagtta caaacgtaga agaactaatg aaaagactag aagaaataaa ggatgctcaa     60
aagaaatttg ctacatatac tcaagaacaa gtggatgaaa ttttagaca agcagctatg    120
gcagctaata gtgctagaat agaactagct aaaatggcag tagaagaaag cggaatggga    180
attgtagaag acaaggttat taaaaatcac tttgcttcag aatatatata taacaaatat    240
aaggatgaaa aaacctgtgg agttttagag agatgatcag gctttggtat agttagaatt    300
gcggaacctg taggagttat tgcagcagta gttccaacaa ctaatccaac atctacagca    360
atatttaaat cactaataga ctttaaaaact agaaatggta aatttttttc accccatcca    420
agggcaaaga aatcaactat tgcagcagct aaaaagtac ttgacgctgc agttaaagct    480
ggtgctcctg aaggaattat aggatggata gatgaaccct tcattgaact ttcacaggtg    540
gtaatgggag aagcaaattt aattcttgca actggtggtc cgggtatggt taaggctgcc    600
tattcttcag gcaaacctgc tgtgggagtt ggtccaggta cacacctgc tgtaattgat    660
gaaagtgccg acattaaaat ggcagtaaat tcaatattac tatcaaaaac ttttgataat    720
ggtatgattt gtgcctcaga gcagtcagta atagttttag actcaatata tgaggaagtt    780
aaaaagaat ttgcttatag gggtgcttat atattaagta aggatgaaac agataaggtt    840
ggaaaaataa tttttaaaaa tggagcctta atgcaggta ttgtaggaca acctgctttt    900
aaaatagcac agctggcagg agtggatgta ccagaaaaag ctaaagtact tataggagag    960
gtagaatcgg tagaacttga agaaccattt tctcatgaaa agttatctcc agttttagct   1020
atgtacaggg caagaattt tgaggatgcc attgcaaaa ctgataaact ggttaggca   1080
ggtggatttg gacatacatc ttcattgtat ataaatccaa tgacagaaaa agcaaagta   1140
gaaaattta gtactatgat gaaaacatca agaactaaaa ttaacacacc ttcatccaa   1200
ggtgtatag gtgatatata taactttaaa ctagctcctt ctttgaacatt aggctgcgt   1260
tcctggggg gaattctgt atccgaaaat gttgggccta acatttattt aaacataaaa   1320
agtgttgctg agaggagaga aaatatgctt tggtttagag taacctgaaaa ggtttatttc   1380
aaaatggta gtcttggagt tgcattaaaa gagttaaaag ttatgaataa gagaaagta   1440
tttatagtaa cagataagt tctttatcaa ttaggttatg tggacaaagt tacaaaagtt   1500
cttgaggaac taaaaatttc ctataaggta tttacagatg tagaaaccaga tccaaccctt   1560
gctacagcta aaaaggtgc agcagaactg ctttcctatg aaccggatac aattatatca   1620
gttggtggtg gttcagcaat ggatgcagct aagatcatgt gggtaatgta tgagcatcca   1680
gaagtaaaat ttgaagattt agctatgaga ttttatgatta taagaaagag agtatatgtt   1740
ttccctaaga tgggagaaaaa ggcaatgatg attcagtag caacatccgc aggaacagg   1800
tcggaagtta ctccatttgc agtaatcact gatgaaaaaa caggagcta aatccattca   1860
gctgattatg aactaactcc agacatggct atagttgatg cagaacttat gatgggaatg   1920
ccaagaggac ttacagcagc ttcgggtata gatgcattaa cccatgcact ggaggctat   1980
gtgtcaataa tggctacaga atttaccaat ggattagccc ttgaagcagt aaagttgata   2040
tttgaatatt taccaaaagc ttatacaaga ggtacaacta tgtaaaggc aagagaaaag   2100
atggctcatg cttcatgtat tgcaggtatg gcctttgcaa atgcattttt aggggtatgc   2160
cactctatgg cacataaatt gggagcacag catcacatac cacatggaat gccaatgca   2220
cttatgatag atgaagttat aaaattcaat gctgtagatg atccaataaa acaagctgca   2280
tttccccaat acgagtatcc aaatgctagg tatagatatg ctcagatagc tgattgtctg   2340
aacttgggag gaaatacaga agagggaaag gtacaactat taataaatgc tatagatgat   2400
ttaaaagcta agtaaatat tccagaaact ataaagaag caggagtttc agaagataaa   2460
ttctatgcta ctttagataa aatgtcagaa ttagcttttg atgatcagtg tacaggagct   2520
aatccaagat atccactgat aagtgaaata aaacaaatgt atataaatgt ttttgataaa   2580
accgaaccaa ttgtagaaga tgaagaaaag taa                                 2613

SEQ ID NO: 6         moltype = DNA  length = 2634
FEATURE              Location/Qualifiers
misc_feature         1..2634
                     note = adhE2, Clostridium autoethanogenum
source               1..2634
                     mol_type = other DNA
                     organism = synthetic construct
SEQUENCE: 6
atgaaggtaa ctaaggtaac taacgttgaa gaattaatga aaagttaga tgaagtaacg     60
gctgctcaaa gaaatttttc tagctatact caagaacaag tggatgaaat ttcaggcag    120
gcagctatgg cagccaatag tgctagaata gacttagcta aaatggcagt ggaagaaagc    180
ggaatgggaa ttgtagaaga caaggtcatt aaaaatcatt ttgttgcaga atatatatat    240
```

-continued

```
aacaaatata agggtgaaaa gacctgcgga gttctggaac aagatgaagg ctttggtatg   300
gttagaattg cagaacctgt aggagttatt gcagcagtag ttccaacaac taatccaaca   360
tctacagcaa tatttaaatc actaatagct ttaaaaacta gaaatggtat agttttttca   420
ccacatccaa gggcaaaaaa atcaactatt gcagcagcta agatagtact tgatgcagca   480
gttaaagctg gtgcccctga aggaattata ggctggatag atgaaccttc tattgaactt   540
tcacaggtgg taatgaaaga agcagatcta attcttgcaa ctggtggacc aggtatggtt   600
aaggctgcct attcttcagg aaagcctgct ataggagttg gtccaggtaa tacacctgct   660
gtaattgatg aaagtgccga cattaaaatg gcagtaaatt caatactact ttcaaaaact   720
tttgataatg gtatgatttg tgcttcagag cagtcagtaa tagttgcaag ctcaatatac   780
gatgaagtca agaaagagtt tgcagataga ggagcatata tattaagtaa ggatgaaaca   840
gataaggttg gaaaaacaat catgattaat ggagctttaa atgctggaat tgtagggcaa   900
agtgccttta aaatagctca gatggcggga gtcagtgtac cggaagatgc taaaatactt   960
ataggagaag ttaaatcggt agaacctgaa gaagagccct ttgctcatga aaagctgtct  1020
ccagttctag ccatgtacaa agcaaaagat tttgatgaag cacttctaaa ggctggaata  1080
ttagttgaac gaggtggaat agggcataca tctgtattgt atgtaaattc gatgacggaa  1140
aaagtaaaag tagaaaagtt cagagaaact atgaagaccg tagaacatt gataaatatg  1200
ccttcagcgc aaggcgctct aggagatata tataacttta aactagctcc ttctttgaca  1260
ttaggctgtg gttcctgggg aggaaactct gtatcagaaa atgttggacc taaacatttg  1320
ttaaacataa agagtgttgc tgagaggaga gaaaatatgc tttggtttag agtacctgaa  1380
aaggtttatt tcaaatatgg cagccttgga gttgcactaa aagaactgag aattatggag  1440
aagaaaaagg cgtttatagt aacgcataaa gttctttatc aattaggtta tgtagataaa  1500
attacaaaga acctcgatga attaagagtt tcatataaaa tatttacaga tgtagaacca  1560
gatccaaccc ttgctacagc taaaaaaggt gcagcagaac tgctttccta tgaaccagat  1620
acaattatag cagttggtgg tggttcggca atggatgctg ccaagatcat gtgggtaatg  1680
tatgagcatc cagaagtaag atttgaagat ttggccatga gatttatgga tataagaaag  1740
agagtatatg tttttcctaa gatgggaaaa aaggcaatga tgatttcagt agcaacatcc  1800
gcaggaacag ggtcagaagt tactccattt gcagtaatta cggacgaaag aacaggagct  1860
aaatatcctc tggctgatta tgaattaact ccaaacatgg ctagttgaa tgcagaactt  1920
atgatgggaa tgcaaagggg gctaacagca gcttcaggta tagatgcgtt gactcatgca  1980
ctggaggcct atgtgtcaat aatgcttcaa gaatatacca acggattggc tcttgaagca  2040
acaagattag tattcaaata tttgccaata gcttatacag aaggtacaat taatgtaaag  2100
gcaagagaaa aaatggctca tgcttcatgt attgcaggta tggcctttgc caatgcattt  2160
ttaggggtat gccactctat ggcacataaa ttgggagcac agcaccacat accacatgga  2220
attgccaatg cacttatgat agatgaagtt ataaaattca atgctgtaga ggctccaagg  2280
aaacaagcgg catttccaca atataaatat ccaaatgtta aagaagata tgctagaata  2340
gctgattacc taaatttagg tggaagtaca gatgatgaaa aagtacaatt gctaataaat  2400
gctatagatg acttaaaaac taagttaaat attccaaaga ctattaaaga agcaggagtt  2460
tcagaagata aattctatgc tactttagat acaagtcag aactggcttt tgatgatcaa  2520
tgtacaggag ctaatcccacg atatccacta ataggagaaa taaaacaaat gtatataaat  2580
gcatttgata caccaaaggc aactgtgag aagaaaacaa gaagaaaaa gtaa          2634

SEQ ID NO: 7          moltype = DNA   length = 5398
FEATURE               Location/Qualifiers
misc_feature          1..5398
                      note = adhE1+adhE2 including intergeneric region,
                      Clostridium autoethanogenum
source                1..5398
                      mol_type = other DNA
                      organism = synthetic construct
SEQUENCE: 7
atgaaagtta caaacgtaga agaactaatg aaaagactag aagaaataaa ggatgctcaa    60
aagaaatttg ctacatatac tcaagaacaa gtggatgaaa ttttagaca agcagctatg   120
gcagctaata gtgctagaat agaactagct aaaatggcag tagaagaaag cggaatggga   180
attgtagaag acaaggttat taaaaatcac tttgcttcag aatatatata taacaaatat   240
aaggatgaaa aaacctgtgg agttttagag agagatgcag gctttggtat agttagaatt   300
gcggaacctg taggagttat tgcagcagta gttccaacaa ctaatccaac atctacagca   360
atatttaaat cactaatagc tttaaaaact agaaatggta aatttttc accccatcca   420
agggcaaaga aatcaactat tgcagcagct aaaatagtac ttgacgctgc agttaaagct   480
ggtgctcctg aaggaattat aggatggata gatgaaccttccattgaact ttcacaggtg   540
gtaatgggag aagcaaattt aattcttgca actggtggtc cgggtatggt taaggctgcc   600
tattcttcag gcaaacctgc tgtgggagtt ggtccaggta acacacctgc tgtaattgat   660
gaaagtgccg acattaaaat ggcagtaaat tcaatattac tatcaaaaac ttttgataat   720
ggtatgattt gtgcctcaga gcagtcagta atagttttag actcaatata tgaggaagtt   780
aaaaaagaat ttgcttatag gggtgcttat atattaagta aggatgaaac agataaggtt   840
ggaaaaataa ttttaaaaaa tggagcctta aatgcaggta ttgtaggaca acctgctttt   900
aaaatagcac agctggcagg agtgcatgta ccagaaaaag ctaaagtact tataggagag   960
gtagaatcgg tagaacttga agaaccattt tctcatgaaa agttatctcc agttttagct  1020
atgtacaggg caagaaatt tgaggatgcc attgcaaaaa ctgataaact ggtagggca  1080
ggtgggttgt gacatacatc ttcattgtat ataatccaa tgacagaaaa agcaaagta  1140
gaaaaattta gtactatgat gaaaacatca agaactataa ttaacacacc ttcatccaa   1200
ggtggtatag gtgatatata aactttaaa ctagctcctt ctttgacatt aggctgcggt  1260
tcctgggggg gaaattctgt atccgaaaat gttgggccta acatttatt aaacataaa   1320
agtgttgctg agaggagaga aaatatgctt tggtttagag tacctgaaaa ggtttattc  1380
aaatatggta gtcttggagt tgcattaaaa gagttaaaag ttataagaga gaaaagta   1440
tttatagtaa cagataaagt tctttatcaa ttaggttatg tggacaaagt tacaaagtt  1500
cttgaggaac taaaaatttc ctataagtta tttacagatg tagaaccaga tccaaccctt  1560
gctacagcta aaaaaggtgc agcagaactg ctttcctatg aaccggatac aattatatca  1620
gttggtggtg gttcagcaat ggatgcagct aagatcatgt gggtaatgta tgagcatcca  1680
gaagtaaaat ttgaagattt agctatgaga tttatggata taagaaagag agtatatgtt  1740
```

```
ttccctaaga tgggagaaaa ggcaatgatg atttcagtag caacatccgc aggaacaggg    1800
tcggaagtta ctccatttgc agtaatcact gatgaaaaaa caggagctaa atatccatta    1860
gctgattatg aactaactcc agacatggct atagttgatg cagaacttat gatgggaatg    1920
ccaagaggac ttacagcagc ttcgggtata gatgcattaa cccatgcact ggaggcgtat    1980
gtgtcaataa tggctacaga atttaccaat ggattagccc ttgaagcagt aaagttgata    2040
tttgaatatt taccaaaagc ttatacagaa ggtacaacta atgtaaaggc aagagaaaag    2100
atggctcatg cttcatgtat tgcaggtatg gcctttgcaa atgcattttt aggggtatgc    2160
cactctatgg cacataaatt gggagcacag catcacatac cacatggaat tgccaatgca    2220
cttatgatag atgaagttat aaaattcaat gctgtagatg atccaataaa acaagctgca    2280
tttccccaat acgagtatcc aaatgctagg tatagatatg ctcagatagc tgattgtctg    2340
aacttgggag gaaatacaga agaggaaaag gtacaactat taataaatgc tatagatgat    2400
ttaaaagcta agttaaatat tccagaaact ataaaagaag caggagtttc agaagataaa    2460
ttctatgcta ctttagataa aatgtcgaaa ttagcttttg atgatcagtg tacaggagct    2520
aatccaagat atccactgat aagtgaaata aaacaaatgt atataaatgt ttttgataaa    2580
accgaaccaa ttgtagaaga tgaagaaaag taattattaa ataaaaatgg tgttcaaata    2640
aaatttgaac accattttta tttttaagga gtaaatatga ataataataa catagaaaca    2700
aacaataaaa atgagaaatt tgtttatatt taacagcata aaaaataaga aagaggtgtc    2760
attaatgaag gtaactaagg taactaacgt tgaagaatta atgaaaagt tagatgaagt    2820
aacggctgct caaaagaaat tttctagcta tactcaagaa caagtggatg aaattttcag    2880
gcaggcagct atggcagcca atagtgctag aatagactta gctaaaatgg cagtggaaga    2940
aagcggaatg gaattgtag aagacaaggt cattaaaaat catttgttg cagaatatat    3000
ataaacaaa tataagggtg aaaagacctg cggagttctg gaacaagatg aaggctttgg    3060
tatggttaga attgcagaac ctgtaggagt tattgcagca gtagttccaa caactaatcc    3120
aacatctaca gcaatattta aatcactaat agctttaaaa actagaaatg gtatagttt    3180
ttcaccacat ccaagggcaa aaaaatcaac tattgcagca gctaagatag tacttgatgc    3240
agcagttaaa gctggtgccc ctgaaggaat tataggctgg atagatgaac cttctattga    3300
actttcacag gtggtaatga aagaagcaga tctaattctt gcaactggtg gaccaggtat    3360
ggttaaggct gcctattctt caggaaagcc tgctatagga gttggtccag gtaatacacc    3420
tgctgtaatt gatgaaagtg ccgacattaa atggcagta aattcaatac tactttcaaa    3480
aactttgat aatggtatga tttgtgcttc agagcagtca gtaatagttg caagctcaat    3540
atacgatgaa gtcaagaaag agtttgcaga tagaggagca tatatattaa gtaaggatga    3600
aacagataag gttggaaaaa caatcatgat taatggagct ttaaatgctg gaattgtagg    3660
gcaaagtgcc tttaaaatag ctcagatggc gggagtcagt gtaccggaag atgctaaaat    3720
acttatagga gaagttaaat cggtagaacc tgaagaagag ccctttgctc atgaaaagct    3780
gtctccagtt ctagccatgt acaaagcaaa agatttgat gaagcacttc taaaggctgg    3840
aagattagtt gaacgaggtg aataggca tacatctgta ttgtatgtaa attcgatgac    3900
ggaaaaagta aaagtagaaa agttcagaga aactatgaag accggtagaa cattgataaa    3960
tatgccttca gcgcaaggcg ctataggaga tatatataac tttaaactag ctccttcttt    4020
gacattaggc tgtggttcct ggggaggaaa ctctgtatca gaaaatgttg gacctaaaca    4080
tttgttaaac ataaagagtg ttgctgagag gagagaaaat atgctttggt ttagagtacc    4140
tgaaaaggtt tatttcaaat atggcagcct tggagttgca ctaaaagaac tgaaattat    4200
ggagaagaaa aaggcgttta tagtaacgga taaagttctt tatcaattag gttatgtaga    4260
taaaattaca aagaacctcg atgaattaag agtttcatat aaaatattta cagatgtaga    4320
accagatcca accettgcta cagctaaaaa aggtgcagca gaactgctt cctatgaacc    4380
agatacaatt atagcagttg gtggtggttc ggcaatggat gctgccaaga tcatgtgggt    4440
aatgtatgag catccagaag taagatttga agatttggcc atagagatta tggatataag    4500
aaagagagta tatgtttttc ctaagatggg agaaaaggca atgatgattt cagtagcaac    4560
atccgcagga acagggtcag aagttactcc atttgcagta attacggacg aaagaacagg    4620
agctaaatat cctctggctg attatgaatt aactccaaac atggctatag ttgatgcaga    4680
acttatgatg ggaatgccaa aggggctaac agcagcttgg gtatagatg cgttgactca    4740
tgcactggag gcctatgtgt caataatggc ttcagaatat accaacggat tggctcttga    4800
agcaacaaga ttagtattca aatatttgcc aatagcttat acagaaggta caattaatgt    4860
aaaggcaaga gaaaaatgg ctcatgcttc atgtattgca ggtatggcct ttgccaatgc    4920
attttaggg gtatgccact ctatggcaca taaattggga gcacagcacc acataccaca    4980
tggaattgcc aatgcactta tgatagtga agttataaaa ttcaatgctg tagaggctcc    5040
aaggaaacaa gcggcatttc cacaatataa atatccaaat gttaaagaa gatgctag    5100
aatagctgat tacctaaatt taggtgaag tacagatgat gaaaaagtac aattgctaat    5160
aaatgctata gatgacttaa aaactaagtt aatatttcca aagactatta agaagcagg    5220
agtttcagaa gataaattct atgctacttt agatacaatg tcagaactgg cttttgatga    5280
tcaatgtaca ggagctaatc cacgatatcc actaatagga gaaataaaac aaatgtatat    5340
aaatgcattt gatacaccaa aggcaactgt ggagaagaaa acaagaaaga aaaagtaa    5398
```

SEQ ID NO: 8    moltype = DNA length = 500
FEATURE    Location/Qualifiers
misc_feature   1..500
         note = Region containing PadhE1/E2 promoter, Clostridium
         autoethanogenum
source     1..500
         mol_type = other DNA
         organism = synthetic construct
SEQUENCE: 8

```
atatccacta aaaaaataaa attataataa aaaatacaaa aaaataattg acaatatata     60
aataattatg cataattata tcatgataac aattagttaa gcataattac atatatatga    120
acataatatg acatcttaga agcatatctt tcgttagtaa taataatt tcctttagaa      180
gaaaatgatt tatttaaaat aaatagtgta atgtttttta taatttcaaa aagttcccca    240
attagcata ctaggcatga taaaaatagc ttgaataagt gcttgctatt atttattgat     300
acatagagaa tttcactctt tgcattttat ctaacatcaa ggggttatt tgtcacaaat    360
```

```
tatgtaaaaa taaaacaaag atgtaagaaa atcctatgat ataaattttg taaacataat    420
aaattagctt tgataagatt ggaagaatga tagttactac ttagaactgc taaaaattag    480
gaaagaggtg tcgctaatta                                                500
```

MICROORGANISM WITH KNOCK-IN AT ACETOLACTATE DECARBOXYLASE GENE LOCUS

CROSS REFERENCE TO RELATED APPLICATIONS

This application is a divisional of U.S. patent application Ser. No. 17/303,677, filed Jun. 4, 2021, which claims the benefit of U.S. Provisional Patent Application No. 63/035,739 filed Jun. 6, 2020, the entirety of which is incorporated herein by reference.

GOVERNMENT RIGHTS

This disclosure was made with Government support under Assistance Agreement Award No. DE-EE0007566 awarded by the U.S. Department of Energy. The Government has certain rights in this disclosure.

REFERENCE TO A SEQUENCE LISTING

The application contains a Sequence Listing which has been submitted electronically in ST.26 Sequence listing XML format and is hereby incorporated by reference in its entirety. Said ST.26 Sequence listing XML, created on Apr. 28, 2023, is named LT163US2-Sequences.xml and is 24,471 bytes in size.

FIELD

This application relates to genetically engineered microorganisms and use of those microorganisms for the fermentative production of products from substrates comprising carbon dioxide ($CO_2$), carbon monoxide (CO), and/or hydrogen ($H_2$).

BACKGROUND

Mitigation of impending climate change requires drastic reductions in emissions of greenhouse gases (GHGs), such as those generated through the burning of fossil fuels like coal and oil. Although sustainable sources of fuels and chemicals are currently insufficient to significantly displace our dependence on fossil carbon, gas fermentation has recently emerged as an alternative platform for the biological fixation of such gases such as CO, $CO_2$, and/or $H_2$ into sustainable fuels and chemicals. In particular, gas fermentation technology can utilize a wide range of feedstocks including gasified carbonaceous matter (e.g., municipal solid waste or agricultural waste) or industrial waste gases (e.g., from steel mills or oil refineries) to produce ethanol, jet fuel, and a variety of other products. Gas fermentation alone could displace 30% of crude oil use and reduce global $CO_2$ emissions by 10%, but, as with any disruptive technology, many technical challenges must be overcome before this potential is fully achieved.

In particular, there remains a need for additional microorganisms with improved stability for the production of native and nonnative products from gaseous substrates.

DETAILED DESCRIPTION

Figure 1:
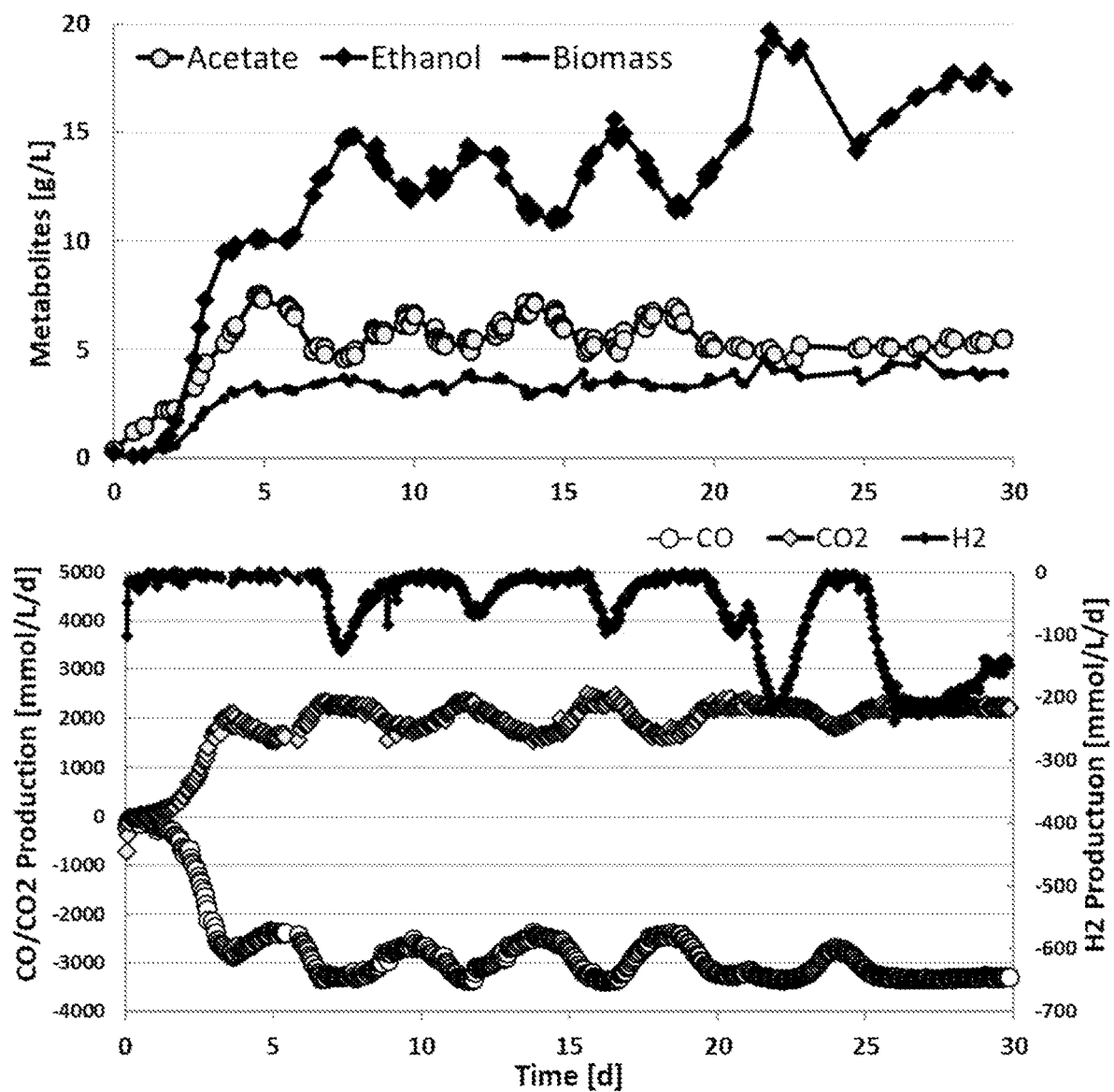
FIG. 1 is a set of graphs depicting fermentation of a microorganism with a disrupted acetolactate decarboxylase gene (ΔbudA) and a disrupted primary-secondary alcohol dehydrogenase gene (ΔsecAdh). The top panel shows metabolite production (ethanol and acetate). The bottom panel shows gas consumption and production (CO, $CO_2$, and $H_2$).

Acetolactate decarboxylase is a key step for formation of 2,3-butanediol (2,3-BDO) (Köpke, Appl Env Microbiol, 80: 3394-3405, 2014) and knocking out this enzyme has been demonstrated to abolish 2,3-BDO production (WO 2013/115659). In order to channel flux towards other heterologous products such as acetone, a knockout of acetolactate decarboxylase would be expected to increase production of those heterologous products.

However, the inventors have found that this is not necessarily the case. In particular, the inventors have discovered that knock-in of genes responsible for the production of heterologous products at the acetolactate decarboxylase locus is key for achieving stable fermentation and high product titers.

Provided is a genetically engineered microorganism comprising knock-in of DNA at an acetolactate decarboxylase gene locus. In one embodiment, the DNA replaces the coding region of the acetolactate decarboxylase gene, either in its entirety or in part. In one embodiment, the DNA does not replace the acetolactate decarboxylase promoter.

In one embodiment, the acetolactate decarboxylase has the activity defined by EC 4.1.1.5, i.e., (S)-2-hydroxy-2-methyl-3-oxobutanoate ←→ (R)-2-acetoin+$CO_2$. In one embodiment, the acetolactate decarboxylase is budA. In one embodiment, the budA comprises SEQ ID NO: 3.

After the knock-in is performed, the microorganism will typically not have a functional acetolactate decarboxylase gene, such that the microorganism will express acetolactate decarboxylase and will not produce products such as 2,3-butanediol.

In one embodiment, the knocked-in DNA encodes one or more enzymes. In one embodiment, these enzyme(s) are nonnative to the microorganism, i.e., not naturally present in the microorganism. In one embodiment these enzyme(s) are native to the microorganism, i.e., naturally present in the microorganism, and simply add another copy of the enzyme (s) into the genome of the microorganism.

In one embodiment, the enzyme(s) encoded by the knocked-in DNA are under the control of an acetolactate decarboxylase promoter, e.g., $P_{budA}$. In one embodiment, the DNA comprises a promoter, such as a $P_{fer}$ promoter. In one embodiment, the enzyme(s) are under the control of both an acetolactate decarboxylase promoter and at least one other promoter. In one embodiment, the enzyme(s) are under the control of both $P_{budA}$ and $P_{fer}$.

In one embodiment, an acetone pathway is knocked-in at the acetolactate decarboxylase gene locus. The acetone pathway may comprise a thiolase, a CoA transferase, and a decarboxylase. In one embodiment, the decarboxylase is acetoacetate decarboxylase or alpha-ketoisovalerate decarboxylase. For example, the acetone pathway may comprise thlA, ctfAB, and adc or thlA, ctfAB, and kivd. If present, a primary-secondary alcohol dehydrogenase, such as secAdh, will convert acetone to isopropanol. Introduction of a disruptive mutation (e.g., a knock-out mutation) in a gene encoding this enzyme will result in the production of acetone whereas expression of this enzyme will result in the production of isopropanol. Accordingly, depending on the genetic background of the host microorganism, introduction of the acetone pathway will result in the production of either acetone or isopropanol. The engineering of microorganisms to produce acetone and isopropanol is described in WO 2012/115527. The engineering of microorganisms to knock-out primary-secondary alcohol dehydrogenase activity is described in WO 2015/085015.

In one embodiment, the microorganism comprises an acetone pathway and also comprises a disruptive mutation in primary-secondary alcohol dehydrogenase gene, such that the microorganism produces acetone. In one embodiment, the microorganism comprises an acetone pathway and also comprises a functional primary-secondary alcohol dehydrogenase, such that the microorganism produces isopropanol.

In fact, the knocked-in DNA may encode essentially any enzyme or enzyme pathway. For example, the enzyme(s) encoded by the knocked-in DNA may enable production of 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, 1,3-hexanediol, 3-methyl-2-butanol, 2-buten-1-ol, isovalerate, isoamyl alcohol, or monoethylene glycol.

In one embodiment, the microorganism is a C1-fixing microorganism. In one embodiment, the microorganism is a Wood-Ljungdahl microorganism. In one embodiment, the microorganism is a bacterium. In one embodiment, the microorganism is a member of a genus selected from *Acetobacterium, Alkalibaculum, Blautia, Butyribacterium, Clostridium, Eubacterium, Moorella, Oxobacter, Sporomusa,* and *Thermoanaerobacter.*

Further provided is a method of producing a product comprising culturing the microorganism in the presence of a gaseous substrate. In one embodiment, the gaseous substrate comprises a C1-carbon source comprising CO, $CO_2$, and/or $H_2$. In one embodiment, the gaseous substrate comprises syngas or industrial waste gas. In one embodiment, the product is 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, choris-mate-derived products, 3-hydroxybutyrate, 1,3-butanediol, 2-hydroxyisobutyrate or 2-hydroxyisobutyric acid, isobutylene, adipic acid, 1,3-hexanediol, 3-methyl-2-butanol, 2-buten-1-ol, isovalerate, isoamyl alcohol, or monoethylene glycol.

DEFINITIONS AND BACKGROUND

Unless otherwise defined, the following terms as used throughout this specification are defined as follows:

The term "fermentation" should be interpreted as a metabolic process that produces chemical changes in a substrate. For example, a fermentation process receives one or more substrates and produces one or more products through utilization of one or more microorganisms. The term "fermentation," "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

Metabolic engineering of microorganisms, such as *Clostridia*, can tremendously expand their ability to produce many important fuel and chemical molecules other than native metabolites, such as ethanol. However, until recently, *Clostridia* were considered genetically intractable and therefore generally off limits to extensive metabolic engineering efforts. In recent years several different methods for genome engineering for *Clostridia* have been developed including intron-based methods (ClosTron) (Kuehne, *Strain Eng: Methods and Protocols,* 389-407, 2011), allelic exchange methods (ACE) (Heap, *Nucl Acids Res,* 40: e59, 2012; Ng,

*PLoS One*, 8: e56051, 2013), Triple Cross (Liew, *Frontiers Microbiol*, 7: 694, 2016), methods mediated through I-SceI (Zhang, *Journal Microbiol Methods*, 108: 49-60, 2015), MazF (Al-Hinai, *Appl Environ Microbiol*, 78: 8112-8121, 2012), or others (Argyros, *Appl Environ Microbiol*, 77: 8288-8294, 2011), Cre-Lox (Ueki, mBio, 5: e01636-01614, 2014), and CRISPR/Cas9 (Nagaraju, Biotechnol Biofuels, 9: 219, 2016). However, it remains extremely challenging to iteratively introduce more than a few genetic changes, due to slow and laborious cycling times and limitations on the transferability of these genetic techniques across species. Furthermore, we do not yet sufficiently understand C1 metabolism in *Clostridia* to reliably predict modifications that will maximize C1 uptake, conversion, and carbon/energy/redox flows towards product synthesis. Accordingly, introduction of target pathways in *Clostridia* remains a tedious and time-consuming process.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived. In one embodiment, the expression of an endogenous gene may be controlled by an exogenous regulatory element, such as an exogenous promoter.

"Exogenous" refers to a nucleic acid or protein that originates outside the microorganism of the disclosure. For example, an exogenous gene or enzyme may be artificially or recombinantly created and introduced to or expressed in the microorganism of the disclosure. An exogenous gene or enzyme may also be isolated from a heterologous microorganism and introduced to or expressed in the microorganism of the disclosure. Exogenous nucleic acids may be adapted to integrate into the genome of the microorganism of the disclosure or to remain in an extra-chromosomal state in the microorganism of the disclosure, for example, in a plasmid.

"Heterologous" refers to a nucleic acid or protein that is not present in the wild-type or parental microorganism from which the microorganism of the disclosure is derived. For example, a heterologous gene or enzyme may be derived from a different strain or species and introduced to or expressed in the microorganism of the disclosure. The heterologous gene or enzyme may be introduced to or expressed in the microorganism of the disclosure in the form in which it occurs in the different strain or species. Alternatively, the heterologous gene or enzyme may be modified in some way, e.g., by codon-optimizing it for expression in the microorganism of the disclosure or by engineering it to alter function, such as to reverse the direction of enzyme activity or to alter substrate specificity.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide", "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited, to the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the disclosure compared to the wild-type or parental microorganism from which the microorganism of the disclosure is derived. In one embodiment, the mutation may be a deletion, insertion, or substitution in a gene encoding an enzyme. In another embodiment, the mutation may be a deletion, insertion, or substitution of one or more amino acids in an enzyme.

In particular, a "disruptive mutation" is a mutation that reduces or eliminates (i.e., "disrupts") the expression or activity of a gene or enzyme. The disruptive mutation may partially inactivate, fully inactivate, or delete the gene or enzyme. The disruptive mutation may be any mutation that reduces, prevents, or blocks the biosynthesis of a product produced by an enzyme. The disruptive mutation may be a knockout (KO) mutation. The disruption may also be a knockdown (KD) mutation that reduces, but does not entirely eliminate, the expression or activity of a gene, protein, or enzyme. While KOs are generally effective in increasing product yields, they sometimes come with the penalty of growth defects or genetic instabilities that outweigh the benefits, particularly for non-growth coupled products. The disruptive mutation may include, for example, a mutation in a gene encoding an enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, siRNA, CRISPR) or protein which inhibits the expression of an enzyme. The disruptive mutation may be introduced using any method known in the art.

Introduction of a disruptive mutation results in a microorganism of the disclosure that produces no target product or substantially no target product or a reduced amount of target product compared to the parental microorganism from which the microorganism of the disclosure is derived. For example, the microorganism of the disclosure may produce no target product or at least about 1%, 3%, 5%, 10%, 20%, 30%, 40%, 50%, 60%, 70%, 80%, 90%, or 95% less target product than the parental microorganism. For example, the microorganism of the disclosure may produce less than about 0.001, 0.01, 0.10, 0.30, 0.50, or 1.0 g/L target product.

"Knock-in" refers to a genetic engineering method that involves the substitution of DNA in a genetic locus or the insertion of new DNA in a genetic locus. Often, a knock-in will replace a gene with one or more different genes. For instance, an acetolactate decarboxylase (budA) gene may be replaced in whole or in part with one or more different genes. In one embodiment, only the coding region of the gene is replaced. In one embodiment, the entire operon for the gene is replaced, including any promoter regions.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the disclosure are codon optimized for expression in *Clostridium*, particularly *Clostridium autoethanogenum*, *Clostridium ljungdahlii*, or *Clostridium ragsdalei*. In a further preferred embodiment, the genes of the disclosure are codon optimized for expression in *Clostridium autoethanogenum* LZ1561, which is deposited under DSMZ accession number DSM23693.

"Overexpressed" refers to an increase in expression of a nucleic acid or protein in the microorganism of the disclosure compared to the wild-type or parental microorganism from which the microorganism of the disclosure is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate:ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archaeon, virus, or fungus. The microorganism of the disclosure is typically a bacterium. As used herein, recitation of "microorganism" should be taken to encompass "bacterium."

A "parental microorganism" is a microorganism used to generate a microorganism of the disclosure. The parental microorganism may be a naturally-occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited with Deutsche Sammlung von Mikroorganismen and Zellkulturen GmbH (DSMZ) located at Inhoffenstraße 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum*, *Clostridium ljungdahlii*, or *Clostridium ragsdalei*. In a preferred embodiment, the microorganism of the disclosure is derived from *Clostridium autoethanogenum* LZ1561, which is deposited under DSMZ accession number DSM23693.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, and/or a methanotroph. Table 1 provides a representative list of microorganisms and identifies their functional characteristics.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, CO2, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1 carbon source. Typically, the microorganism of the disclosure is a C1-fixing bacterium. In a preferred embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the disclosure is an anaerobe. In a preferred embodiment, the microorganism of the disclosure is derived from an anaerobe identified in Table 1.

TABLE 1

|  | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/−[1] | + | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/−[2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | −[3] | + | + |
| *Oxobacter pfennigii* | + | + | + | + | − | + | + |
| *Sporomusa ovata* | + | + | + | + | − | + | +/−[4] |
| *Sporomusa silvacetica* | + | + | + | + | − | + | +/−[5] |
| *Sporomusa sphaeroides* | + | + | + | + | − | + | +/−[6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, NY, 2006). All naturally occurring acetogens are C1-fixing, anaerobic, autotrophic, and non-methanotrophic. Typically, the microorganism of the disclosure is an acetogen. In a preferred embodiment, the microorganism of the disclosure is derived from an acetogen identified in Table 1.

An "ethanologen" is a microorganism that produces or is capable of producing ethanol. Typically, the microorganism of the disclosure is an ethanologen. In a preferred embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the disclosure is an autotroph. In a preferred embodiment, the microorganism of the disclosure is derived from an autotroph identified in Table 1.

A "carboxydotroph" is a microorganism capable of utilizing CO as a sole source of carbon and energy. Typically, the microorganism of the disclosure is a carboxydotroph. In a preferred embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

More broadly, the microorganism of the disclosure may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa*, and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides*, and *Thermoanaerobacter kivui*.

In a preferred embodiment, the microorganism of the disclosure is derived from the cluster of *Clostridia* comprising the species *Clostridium autoethanogenum, Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1 fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum, Clostridium ljungdahlii*, or *Clostridium ragsdalei* are not specific to that species, but are rather general characteristics for this cluster of C1 fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the disclosure may also be derived from an isolate or mutant of *Clostridium autoethanogenum, Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LZ1560 (DSM19630) (WO 2009/064200), and LZ1561 (DSM23693) (WO 2012/015317). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the disclosure. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the disclosure typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

The microorganism of the disclosure may be cultured with the gas stream to produce one or more products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and monoethylene glycol (WO 2019/126400). In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product account for at least about 5%, 10%, 15%, 20%, 30%, 50%, or 75% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition.

One embodiment is a genetically engineered microorganism comprising knock-in of DNA at an acetolactate decarboxylase gene locus.

The microorganism of an embodiment, wherein the DNA replaces the coding region of the acetolactate decarboxylase gene.

The microorganism of an embodiment, wherein the DNA does not replace the acetolactate decarboxylase promoter.

The microorganism of an embodiment, wherein the microorganism does not produce 2,3-butanediol.

The microorganism of an embodiment, wherein the DNA encodes one or more enzymes.

The microorganism of an embodiment, wherein the one or more enzymes are nonnative to the microorganism.

The microorganism of an embodiment, wherein the one or more enzymes are native to the microorganism.

The microorganism of an embodiment, wherein the one or more enzymes are under the control of an acetolactate decarboxylase promoter.

The microorganism of an embodiment, wherein the DNA comprises a promoter.

The microorganism of an embodiment, wherein the one or more enzymes are under the control of both an acetolactate decarboxylase promoter and at least one other promoter.

The microorganism of an embodiment, wherein the one or more enzymes comprise a thiolase, a CoA transferase, and a decarboxylase selected from acetoacetate decarboxylase or alpha-ketoisovalerate decarboxylase.

The microorganism of an embodiment, wherein the microorganism produces one or more of acetone and isopropanol.

The microorganism of an embodiment, wherein the microorganism further comprises a disruptive mutation in a primary-secondary alcohol dehydrogenase gene.

The microorganism of an embodiment, wherein the one or more enzymes enable production of 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, 1,3-hexanediol, 3-methyl-2-butanol, 2-buten-1-ol, isovalerate, isoamyl alcohol, or monoethylene glycol.

The microorganism of an embodiment, wherein the microorganism is a C1-fixing microorganism.

The microorganism of an embodiment, wherein the microorganism is a Wood-Ljungdahl microorganism.

The microorganism of an embodiment, wherein the microorganism is a bacterium.

The microorganism of an embodiment, wherein the microorganism is a member of a genus selected from *Acetobacterium, Alkalibaculum, Blautia, Butyribacterium, Clostridium, Eubacterium, Moorella, Oxobacter, Sporomusa,* and *Thermoanaerobacter.*

One embodiment is a method of producing a product comprising culturing the microorganism of claim 1 in the presence of a gaseous substrate.

The method of an embodiment, wherein the gaseous substrate comprises a C1-carbon source comprising CO, $CO_2$, and/or $H_2$.

The method of an embodiment, wherein the gaseous substrate comprises syngas or industrial waste gas.

The method of an embodiment, wherein the product is 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, 1,3-hexanediol, 3-methyl-2-butanol, 2-buten-1-ol, isovalerate, isoamyl alcohol, or monoethylene glycol.

EXAMPLES

The following examples further illustrate the disclosure but, of course, should not be construed to limit its scope in any way.

Example 1

This example describes a ΔbudAΔsecAdh microorganism.

Acetolactate decarboxylase is a key step for formation of 2,3-butanediol (2,3-BDO) (Köpke, Appl Env Microbiol, 80: 3394-3405, 2014) and knocking out this enzyme has been demonstrated to abolish 2,3-BDO production (WO 2013/115659). In order to channel flux towards other heterologous products such as acetone, a knockout of the respective budA gene was predicted to improve production.

A knock-out of budA in a strain of *C. autoethanogenum* that already contained a primary-secondary alcohol dehydrogenase (secAdh) gene knock-out (ΔsecAdh) (WO 2015/085015) to yield a ΔbudAΔsecAdh strain. Knock-out of budA was carried out as described earlier (WO 2013/115659).

Single colonies were isolated and restreaked to fresh appropriate selection plates and then screened for double crossover events. Confirmed double crossover events which had correct size of PCR product were re-streaked again to ensure plasmid loss. The correct colonies were picked into liquid medium and frozen stocks were prepared. Genotype was confirmed through whole genome sequencing and phenotype was checked through growth studies and continuous stirred tank reactor (CSTR) runs. As shown in FIG. 1, oscillations in metabolite production and gas consumption/production were observed.

Example 2

This example describes a ΔbudAΔsecAdh microorganism that expresses an acetone pathway (thlA, ctfAB, adc) from a plasmid.

The ΔbudAΔsecAdh microorganism of Example 1 was further modified to introduce a plasmid containing an acetone pathway (thlA, ctfAB, adc). This strain produced less acetone than a parent ΔsecAdh strain with the same pathway and under the same growth conditions but without the knock-out of budA. This is surprising since knock-out of budA would have been expected to redirect carbon flux from 2,3-BDO to other metabolites such as acetone and/or ethanol.

Figure 2:
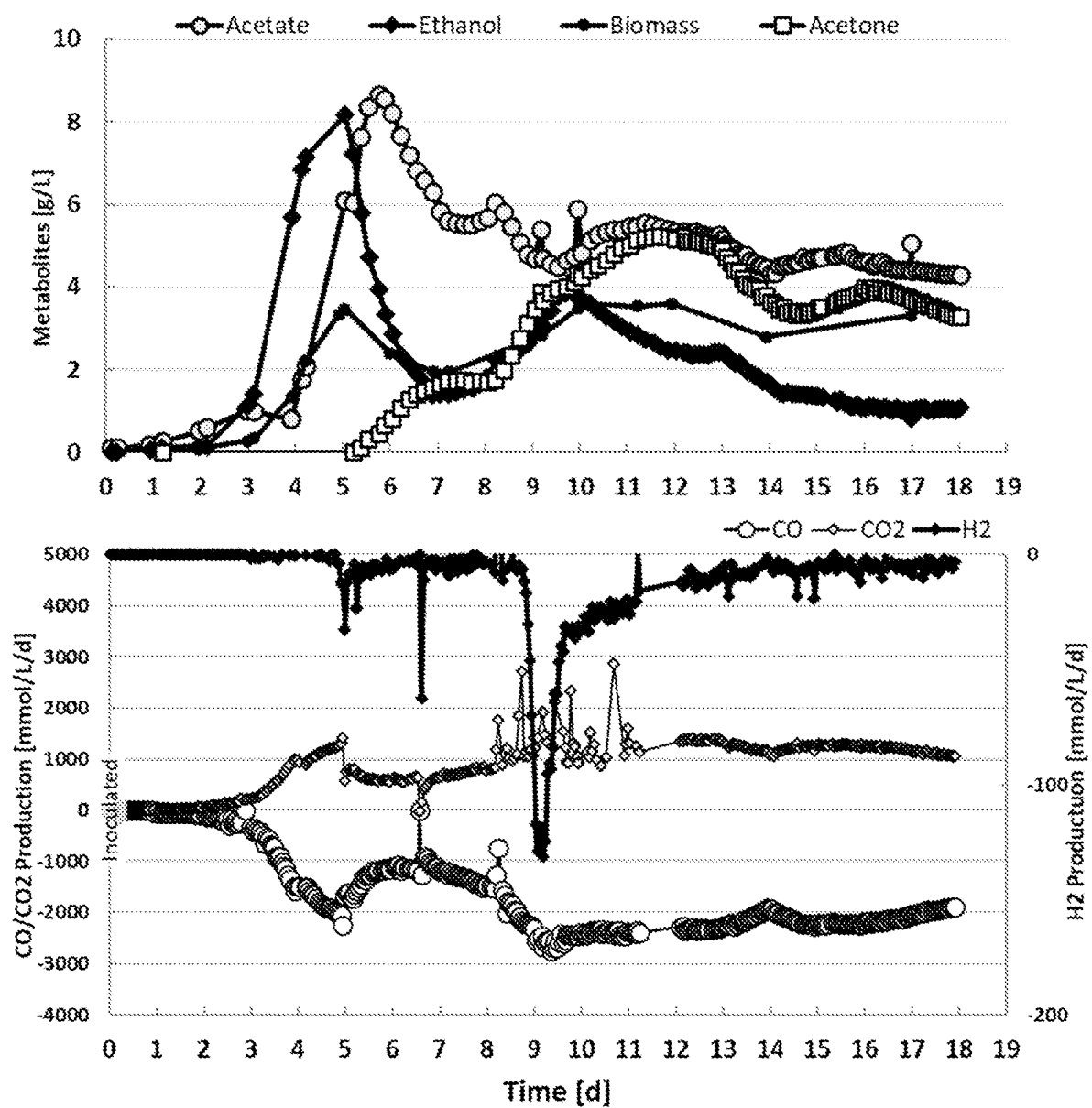
FIG. 2 is a set of graphs depicting fermentation of a ΔbudAΔsecAdh microorganism with expression of an acetone pathway (thlA, ctfAB, adc) on a plasmid. The acetone pathway is under the control of a $P_{fer}$ promoter. The top panel shows metabolite production (ethanol, acetate, and acetone). The bottom panel shows gas consumption and production (CO, $CO_2$, and $H_2$).

Furthermore, this strain did not grow well or demonstrate stable acetone production in a CSTR with a gas mix: 50% CO 10% $H_2$, 30% $CO_2$, balance $N_2$ (FIG. 2). Again, an oscillation pattern was observed during growth: peaks and troughs of production, CO and hydrogen uptake in coordination with troughs and peaks of acetate and $CO_2$ production.

Example 3

This example describes a ΔsecAdh microorganism with knock-in of an acetone pathway (thlA, ctfAB, adc) at an acetolactate decarboxylase (budA) gene locus.

The KI/KO plasmid for acetone pathway knock-in at the budA locus was constructed using the budA KO plasmid as the backbone and the acetone pathway was inserted in between the 5' and 3' budA KO homology arms of the budA KO plasmid. The acetone pathway contained thlA, ctfAB, and adc under the control of the Pfer promoter. The complete KI/KO plasmid was assembled using GeneArt Seamless Cloning and Assembly Kit (ThermoFisher Scientific). The correct KI/KO plasmid was PCR screened and confirmed by sequencing.

The process of obtaining the KI mutant was the same as previously described in constructing the budA KO strain, yielding a ΔbudAΔsecAdh strain with the acetone pathway introduced at the budA locus. PCR screening was carried out and colonies with correct size of PCR product were grown up, genomic DNA isolated and subjected for whole genome DNA sequencing in order to confirm the genotype.

Figure 3:
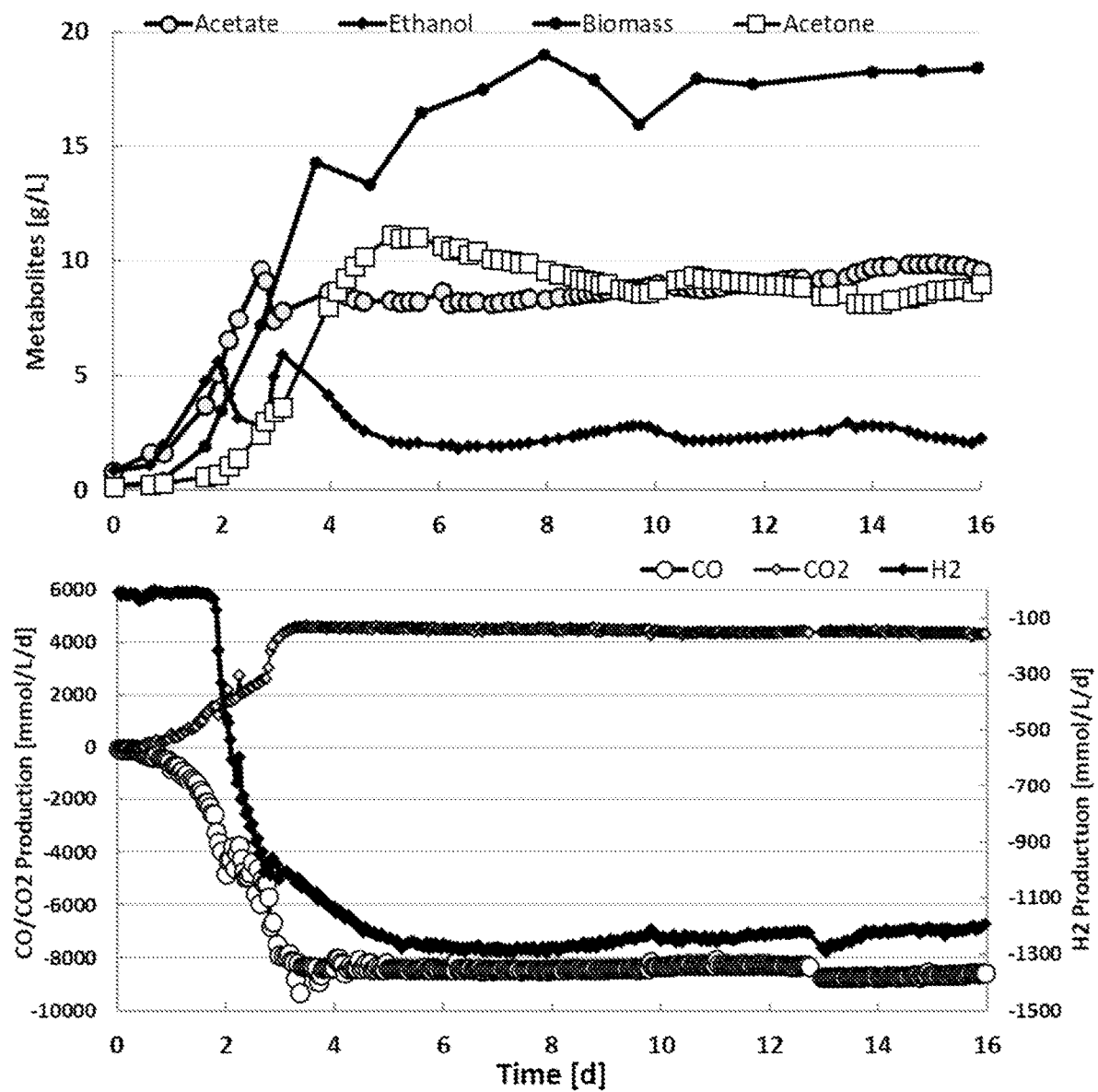
FIG. 3 is a set of graphs depicting fermentation of a ΔsecAdh microorganism with knock-in of an acetone pathway (thlA, ctfAB, adc) at an acetolactate decarboxylase gene (budA) locus. The acetone pathway is under the control of a $P_{budA}$ promoter and a $P_{fer}$ promoter. The top panel shows metabolite production (ethanol, acetate, acetone acetone). The bottom panel shows gas consumption and production (CO, $CO_2$, and $H_2$).

The strain was grown in CSTR with a gas mix: 50% CO 10% $H_2$, 30% $CO_2$, balance $N_2$. The strain grew well and produced high levels of acetone (FIG. 3).

Example 4

This comparative example describes a microorganism with a functional primary-secondary alcohol dehydrogenase (secAdh) and knock-in of an acetone pathway (thlA, ctfAB, adc) at a bifunctional aldehyde-alcohol dehydrogenase (adhE1+adhE2) gene locus. Primary-secondary alcohol dehydrogenase (secAdh) converts acetone to isopropanol, such that this strain produces isopropanol rather than acetone.

The acetone pathway was inserted at the adhE1+adhE2 locus with similar steps as those described above. The homology arms were amplified via PCR and genotype was confirmed via sequencing.

Figure 4:
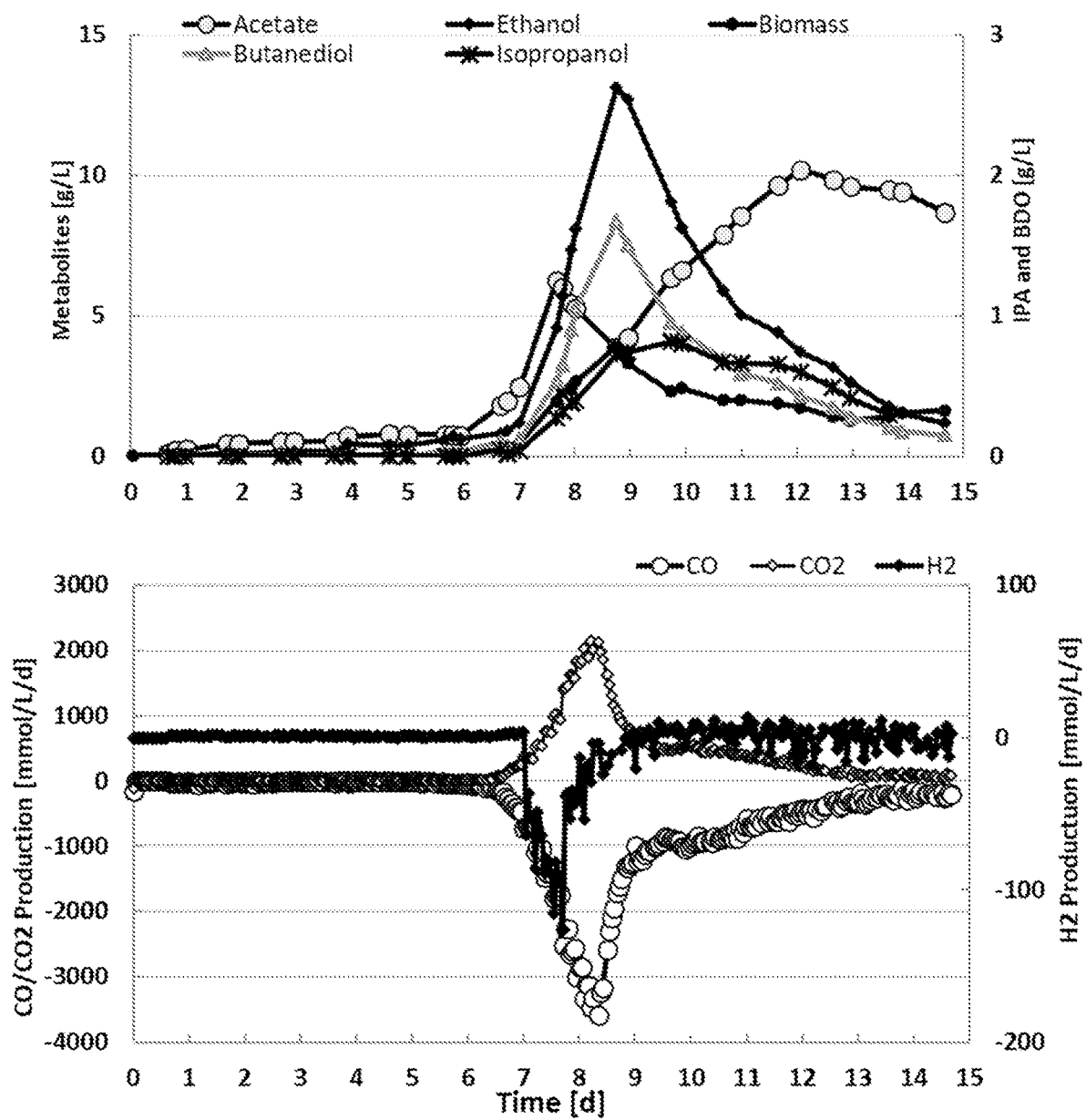
FIG. 4 is a set of graphs depicting fermentation of a microorganism with knock-in of an acetone pathway (thlA, ctfAB, adc) at bifunctional aldehyde-alcohol dehydrogenase (adhE1+adhE2) gene locus and a functional primary-secondary alcohol dehydrogenase (secAdh) gene. Primary-secondary alcohol dehydrogenase (secAdh) converts acetone to isopropanol, such that this strain produces isopropanol rather than acetone. The acetone pathway is under the control of a $P_{adhE1/E2}$ promoter and a $P_{fer}$ promoter. The top panel shows metabolite production (ethanol, acetate, acetone, and isopropanol). The bottom panel shows gas consumption and production (CO, $CO_2$, and $H_2$).

The strain grew poorly in a CSTR and did not produce isopropanol or ethanol well (FIG. 4). It took about 6 days in the reactor to have enough cell biomass for appreciable production of ethanol and isopropanol. The fermentation was not stable over the two-week course of the experiment. Accordingly, knock-in at the adhE1+adhE2 locus does not confer the same benefits as knock-in at the budA locus.

Example 5

This example describes integration of other genes or pathways at the budA locus.

Wood-Ljungdahl microorganisms have already been engineered to produce a variety of nonnative products, including 1-butanol (WO 2008/115080, WO 2012/053905, and WO 2017/066498), butyrate (WO 2008/115080), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and monoethylene glycol (WO 2019/126400). Any of these genes or pathways could be knocked-in at the budA locus to yield a strain with improved performance.

In one embodiment, the knock-in DNA encodes a 3-hydroxybutyrate pathway comprising, e.g., thlA and hbd. In one embodiment, the knock-in DNA encodes an alternative 3-hydroxybutyrate pathway comprising, e.g., thlA, ctfAB, and hbd. In one embodiment, the knock-in DNA encodes a butanol pathway comprising, e.g., thlA, hbd, bcd, and etfAB. In one embodiment, the knock-in DNA comprises a mevalonate pathway comprising, e.g., thlA, HMGS, and HMGR. These pathways may be under the control of one or more promoters, e.g., $P_{budA}$ and/or $P_{fer}$.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavor in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A genetically engineered C1-fixing microorganism comprising knock-in of DNA at an acetolactate decarboxylase gene locus, wherein the microorganism comprises oscillations in metabolite production and gas consumption.

2. The microorganism of claim 1, wherein the DNA replaces the coding region of the acetolactate decarboxylase gene.

3. The microorganism of claim 1, wherein the DNA does not replace the acetolactate decarboxylase promoter.

4. The microorganism of claim 1, wherein the microorganism does not produce 2,3-butanediol.

5. The microorganism of claim 1, wherein the DNA encodes one or more enzymes.

6. The microorganism of claim 5, wherein the one or more enzymes are nonnative to the microorganism.

7. The microorganism of claim 5, wherein the one or more enzymes are native to the microorganism.

8. The microorganism of claim 5, wherein the one or more enzymes are under the control of an acetolactate decarboxylase promoter.

9. The microorganism of claim 1, wherein the DNA comprises a promoter.

10. The microorganism of claim 5, wherein the one or more enzymes are under the control of both an acetolactate decarboxylase promoter and at least one other promoter.

11. The microorganism of claim 5, wherein the one or more enzymes comprise a thiolase, a CoA transferase, and a decarboxylase selected from acetoacetate decarboxylase or alpha-ketoisovalerate decarboxylase.

12. The microorganism of claim 11, wherein the microorganism produces one or more of butadiene and 1-butanol.

13. The microorganism of claim 11, wherein the microorganism further comprises a disruptive mutation in a primary-secondary alcohol dehydrogenase gene.

14. The microorganism of claim 5, wherein the one or more enzymes enable production of 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1 propanol, 1 hexanol, 1 octanol, chorismate-derived products, 3 hydroxybutyrate, 1,3 butanediol, 2-hydroxyisobutyrate or 2-hydroxyisobutyric acid, isobutylene, adipic acid, 1,3 hexanediol, 3-methyl-2-butanol, 2-buten-1-ol, isovalerate, isoamyl alcohol, or monoethylene glycol.

15. The microorganism of claim 1, wherein the microorganism is a Wood-Ljungdahl microorganism.

16. The microorganism of claim 1, wherein the microorganism is a bacterium.

17. The microorganism of claim 1, wherein the microorganism is a member of a genus selected from *Acetobacterium, Alkalibaculum, Blautia, Butyribacterium, Clostridium, Eubacterium, Moorella, Oxobacter, Sporomusa,* and *Thermoanaerobacter.*

18. A method of producing a product comprising culturing the microorganism of claim 1 in the presence of a gaseous substrate.

19. The method of claim 18, wherein the gaseous substrate comprises a C1-carbon source comprising CO, CO2, and/or H2.

20. The method of claim 18, wherein the gaseous substrate comprises syngas or industrial waste gas.

21. The method of claim 18, wherein the product is 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1 propanol, 1 hexanol, 1 octanol, chorismate-derived products, 3 hydroxybutyrate, 1,3 butanediol, 2-hydroxyisobutyrate or 2-hydroxyisobutyric acid, isobutylene, adipic acid, 1,3 hexanediol, 3-methyl-2-butanol, 2-buten-1-ol, isovalerate, isoamyl alcohol, or monoethylene glycol.

\* \* \* \* \*